US012693072B2

(12) United States Patent
Wang et al.

(10) Patent No.: US 12,693,072 B2
(45) Date of Patent: Jul. 28, 2026

(54) ENERGY-SAVING PORTABLE DRYER FOR DIGESTIVE ENDOSCOPE

(71) Applicant: The Second Medical Center, Chinese PLA General Hospital, Beijing (CN)

(72) Inventors: Ming Wang, Beijing (CN); Shiping Xu, Beijing (CN); Hui Shi, Beijing (CN); Hailan Zhu, Beijing (CN)

(73) Assignee: The Second Medical Center, Chinese PLA General Hospital, Beijing (CN)

( * ) Notice: Subject to any disclaimer, the term of this patent is extended or adjusted under 35 U.S.C. 154(b) by 864 days.

(21) Appl. No.: 18/097,518

(22) Filed: Jan. 17, 2023

(65) Prior Publication Data

US 2023/0168035 A1 Jun. 1, 2023

(30) Foreign Application Priority Data

Sep. 6, 2022 (CN) .......................... 202211083389.1

(51) Int. Cl.
*F26B 9/00* (2006.01)
*A61L 2/20* (2026.01)
(Continued)

(52) U.S. Cl.
CPC ................ *F26B 9/003* (2013.01); *A61L 2/20* (2013.01); *A61L 2/26* (2013.01); *F26B 23/10* (2013.01);
(Continued)

(58) Field of Classification Search
CPC ........ F26B 9/003; F26B 23/10; F26B 25/008; A61L 2/20; A61L 2/26; A61L 2202/11;
(Continued)

(56) References Cited

U.S. PATENT DOCUMENTS

2020/0085261 A1 3/2020 Yoo et al.
2020/0118674 A1* 4/2020 Le .......................... A61B 1/121
(Continued)

FOREIGN PATENT DOCUMENTS

CN 108168235 A * 6/2018 .............. F26B 25/10
CN 213312003 U * 6/2021
JP 2009131295 A * 6/2009

OTHER PUBLICATIONS

English translation of CN 108168235 A (Year: 2018).*
English translation of CN 213312003 U (Year: 2021).*
English translation of JP 2009131295 A (Year: 2009).*

*Primary Examiner* — Connor J Tremarche
(74) *Attorney, Agent, or Firm* — Hemisphere Law, PLLC

(57) ABSTRACT

An energy-saving portable dryer for digestive endoscope is disclosed, including a box and a top cover. The box is a hollow shell structure, and the top cover covers the upper port of the box to form a sealed environment. The upper end of the top cover is provided with a controller to control the operation of the device. The box is internally provided with heating tubes. The box is provided with a water inlet and drainage mechanism. The bottom end of the box is provided with a liquid heater to heat the disinfection solution in the box to generate hot vapor. The top cover and the box are installed and disassembled through a fixed mechanism. The energy-saving portable dryer for digestive endoscope has the characteristics of energy saving and high efficiency. And its effect of disinfection and sterilization is better, which increases the practicability.

9 Claims, 6 Drawing Sheets

(51) Int. Cl.

| | |
|---|---|
| *A61L 2/26* | (2006.01) |
| *F26B 23/10* | (2006.01) |
| *F26B 25/00* | (2006.01) |
| *A61L 103/15* | (2026.01) |

(52) U.S. Cl.
CPC ......... *F26B 25/008* (2013.01); *A61L 2103/15* (2026.01); *A61L 2202/11* (2013.01); *A61L 2202/121* (2013.01); *A61L 2202/122* (2013.01)

(58) Field of Classification Search
CPC ......... A61L 2202/121; A61L 2202/122; A61L 2202/24
See application file for complete search history.

(56) References Cited

U.S. PATENT DOCUMENTS

| | | |
|---|---|---|
| 2020/0325621 A1 | 10/2020 | Lee et al. |
| 2021/0404107 A1 | 12/2021 | Bae et al. |

* cited by examiner

ENERGY-SAVING PORTABLE DRYER FOR DIGESTIVE ENDOSCOPE

CROSS REFERENCE TO RELATED APPLICATION

This patent application claims the benefit and priority of Chinese Patent Application No. 202211083389.1 filed on Sep. 6, 2022, the disclosure of which is incorporated by reference herein in its entirety as part of the present application.

TECHNICAL FIELD

The present disclosure relates to the technical field of drying digestive endoscope, and more specifically, to an energy-saving portable dryer for digestive endoscope.

BACKGROUND ART

Digestive endoscope is a group of equipment that can directly obtain images through the digestive tract or obtain ultrasound or X-ray images of the digestive tract and digestive organs through equipment with ultrasound and X-ray to diagnose and treat digestive system diseases. After the digestive endoscope is cleaned, some water remains on the surface of the digestive endoscope, so it needs to be dried before it can be stored. Otherwise, the residual water on the surface of digestive endoscope will cause corrosion on its surface, which will lead to damage of digestive endoscope in the long run. Therefore, it is particularly important to use a drying device after cleaning the digestive endoscope. At present, the existing drying device for digestive endoscope has the following defects.

For example, the working principle of a digestive endoscope drying structure with the application number of CN213066954U is as follows. "The digestive endoscope to be dried is placed on the heat conduction plate and then the box door is closed. At this time, the heating wire, the first motor and the second motor are started to work by controlling the switch. The first motor drives the heat conduction plate to rotate. At the same time, the heat emitted by the heating wire disinfects the digestive endoscope at high temperature through the heat conduction plate. In addition, the second motor drives the second transmission shaft to rotate, and the second transmission shaft drives the fan blades to rotate, generating flowing air to rapidly dry the digestive endoscope with high temperature". It can be seen that the technical solution is to place the digestive endoscope on a rotatable plate, drive the plate through the motor, and then drive the digestive endoscope to rotate, and then realize the purpose of multi angle heating and drying of the digestive endoscope through the heating device. It has the following problems. First, the clamping structure is not set. Since the motor needs to drive the heat conduction plate to rotate, and the digestive endoscope is placed on the heat conduction plate without a clamping structure, it is easy to fall out of the heat conduction plate during rotation, or even seize the heat conduction plate, making it unable to rotate normally Second, as heating and drying is a process of high-temperature sterilization, it will inevitably lead to an increase in pressure. The device is not equipped with a pressure relief structure, which easily leads to gas spraying and injury to users when the box door is opened after use. At the same time, excessive pressure easily leads to internal deformation of the box, which will reduce the service life of the device. Third, the device is equipped with three motors, which has a large power consumption and does not save energy. Fourth, the existing drying device for digestive endoscope lacks a pretreatment structure, which makes it impossible to vapor sterilize the digestive endoscope in advance. The digestive endoscope is directly heated and dried, so that the effect of disinfection and sterilization is not good enough. Therefore, the existing drying structure for digestive endoscope still has many shortcomings, which is worthy of further improvement.

Therefore, an energy-saving portable dryer for digestive endoscope is proposed to solve the problems mentioned above.

SUMMARY

The purpose of the disclosure is to provide an energy-saving portable dryer for digestive endoscope, so as to solve the problems of lack of clamping mechanism, lack of pressure relief mechanism, lack of energy saving and poor effect of disinfection and sterilization proposed by the above background technology in the current market.

To achieve the above purpose, the disclosure provides the following technical solutions. The energy-saving portable dryer for digestive endoscope includes a box and a top cover. The box is a hollow shell structure, and the top cover covers the upper port of the box to form a sealed environment. The upper end of the top cover is provided with a controller to control the operation of the device. And the box is internally provided with heating tubes.

The box is provided with a water inlet and drainage mechanism. The bottom end of the box is provided with a liquid heater. And the liquid heater is arranged to heat a disinfection solution in the box to generate hot vapor.

The top cover and the box are installed and disassembled through a fixed mechanism.

The lower end of the top cover is connected with support plates through a telescopic mechanism, and the upper end of the support plate is provided with a clamp matched with a digestive endoscope. The clamp is arranged to position the digestive endoscope, and the telescopic mechanism drives the support plate to clamp the digestive endoscope for positioning.

Multiple support plates are provided. The bottom end of the support plate at the lowest end is provided with a clamping groove, and the clamping groove and a clamping column at the upper end of the curved disc are mutually matched and inserted.

A partition is also arranged inside the box, and a motor is installed in the partition. The motor is connected with a fan blade and a mixing blade through a driving mechanism to drive the fan blade and the mixing blade to rotate.

The upper end of shaft of the motor is provided with the curved disc, and the curved disc and a crankshaft rod form a reciprocating movement structure. The right end of the crankshaft rod is provided with a piston through a hinge. The surface of the box is provided with an air hole, and the piston moves laterally to open and close the air hole intermittently to achieve intermittent pressure relief.

The air hole is provided with an opening size control mechanism to achieve the efficiency required for regulating the discharge of high-temperature and high-pressure gas.

With the above technical solution, the device can be equipped with a clamping mechanism, which can clamp the digestive endoscope to prevent it from falling off due to rotation during the disinfection and drying process. In addition, the device is equipped with a pressure relief structure, which can adjust and control the pressure inside the box, avoid excessive pressure inside the box, and improve the service life of the device. Only one motor is provided in the device, which can drive the support plate to rotate and simultaneously drive the piston to reciprocate for pressure relief, thus saving energy efficiently. The device can preliminarily use the disinfection solution to sterilize the surface of the digestive endoscope, and the effect of disinfection and sterilization is better.

As the preferred technical solution of the disclosure, the water inlet and drainage mechanism includes a water inlet valve arranged at the lower side of the box, and a drainage valve arranged at the bottom of the box.

With the above technical solution, the device has a water inlet and drainage structure, and can discharge and input liquid by using a valve, so as to facilitate the input and discharge of disinfection solution.

As the preferred technical solution of the disclosure, the fixed mechanism includes a first snap arranged at the lower end of the top cover and a second snap at the side of the box matched with the first snap, so that after the top cover and the box are combined, the first snap and the second snap form a self-locking structure.

With the above technical solution, the device can be convenient to combine and separate the top cover and the box body. The existing snap structure realizes opening and closing, which has low cost and is convenient for use.

As the preferred technical solution of the disclosure, the telescopic mechanism includes a first electric telescopic rod connected with the lower end of the top cover, and the other end of the first electric telescopic rod is connected with the support plate. The support plates are connected to each other through a second electric telescopic rod. The clamping column is a hexagonal prism, and the clamping groove is a hexagonal groove. The surface of the support plate is provided with a mesh for through which the hot vapor passes.

With the above technical solution, the device can be equipped with a clamping structure, and can use the clamp, support plate and electric telescopic rod to clamp the digestive endoscope, so that it can be stably fixed.

As the preferred technical solution of the disclosure, the clamp is an inverted U-shaped block structure. The digestive endoscope is a cylindrical structure, and the radius of the U-shaped part of the clamp is greater than the cylindrical radius of the digestive endoscope.

With the above technical solution, the device can be equipped with a clamping structure, and can position the digestive endoscope by the clamp to avoid shaking.

As the preferred technical solution of the disclosure, the upper end of the top cover is provided with a handle, and the handle is made of thermal insulation material with high temperature resistance.

With the above technical solution, the device is easy to carry. By setting a handle on the upper end of the top cover, the user can easily hold the handle to transport the device.

As the preferred technical solution of the disclosure, the driving mechanism includes a first gear connected with the shaft end of the motor. The surface of the partition is provided with a rotating hole, and the rotating hole is connected with a first gear shaft and a second gear shaft in a rotating manner. The lower end of the first gear shaft is connected with the mixing blade, the upper end of the first gear shaft is connected with the second gear, and the second gear and the second gear shaft form gear mesh. The upper end of the second gear shaft is connected with the fan blade, and the first gear and the second gear form gear mesh.

With the above technical solution, the device can save energy. Only one motor is set, which can drive the support plate to rotate and simultaneously drive the piston to reciprocate for pressure relief, thus achieving energy saving and high efficiency.

As the preferred technical solution of the disclosure, the surface of the piston is provided with a through hole for gas to flow out of the air hole, and the air hole is a square hole structure.

With the above technical solution, the device can be equipped with an exhaust and pressure relief structure, and can use the linkage mechanism to cooperate with the motor to drive the piston to move back and forth, realizing the intermittent opening of the air hole, thereby releasing the pressure inside the box.

As the preferred technical solution of the disclosure, the opening size control mechanism includes a chute arranged on the side of the box, and a sealing plate is arranged in the chute. The sealing plate is located above the through hole and contacts. One end of the sealing plate is connected with the right end of a third electric telescopic rod, and the left end of the third electric telescopic rod is connected with the side of the box. The third electric telescopic rod drives the sealing plate to slide laterally in the chute to adjust the size of the air hole accordingly.

With the above technical solution, the device can conveniently adjust the pressure relief efficiency. The position where the sealing plate blocks the through hole can be adjusted by operating the third electric telescopic rod, so as to realize the volume of gas discharged from each reciprocating.

Compared with the prior art, the disclosure has the following beneficial effects.

1. The energy-saving portable dryer for digestive endoscope is equipped with a clamping mechanism, which can clamp the digestive endoscope with a clamp, a support plate and an electric telescopic rod, so that it can be stably fixed. Thus, it avoids falling off due to rotation during disinfection and drying, and improves the stability. In addition, the device is equipped with a pressure relief structure, which can drive the piston to open intermittently through the linkage mechanism by using the motor to regulate the internal pressure of the box, so as to avoid deformation of the box due to excessive internal pressure, which improves the service life of the device.

2. The energy-saving portable dryer for digestive endoscope has energy-saving characteristics. Only one motor is equipped, which can drive the support plate to rotate and simultaneously drive the piston to reciprocate for pressure relief, thus achieving energy saving and high efficiency. In addition, the device can preliminarily use disinfection solution to sterilize the surface of digestive endoscope, and with the subsequent high-temperature heating sterilization, the effect of disinfection and sterilization is better, which increases the practicability.

Wherein: 1. box; 2. top cover; 201. first electric telescopic rod; 202. second electric telescopic rod; 3. controller; 4. handle; 5. first snap; 501. second snap; 6. water inlet valve; 7. drainage valve; 8. liquid heater; 9. partition; 10. motor; 11. first gear; 12. first gear shaft; 13. second gear; 14. mixing blade; 15. second gear shaft; 16. fan blade; 17. curved disc; 18. clamping column; 19. support plate; 20. clamping groove; 21. mesh; 22. clamp; 23. digestive endoscope; 24. crankshaft rod; 25. piston; 26. through hole; 27. air hole; 28. sealing plate; 29. third electric telescopic rod.

DETAILED DESCRIPTION OF THE EMBODIMENTS

Technical solutions of the present disclosure will be clearly and completely described below with reference to the embodiments. Obviously, the described embodiments are only part of the embodiments of the present disclosure, not all of them.

Embodiment 1

Figure 1:
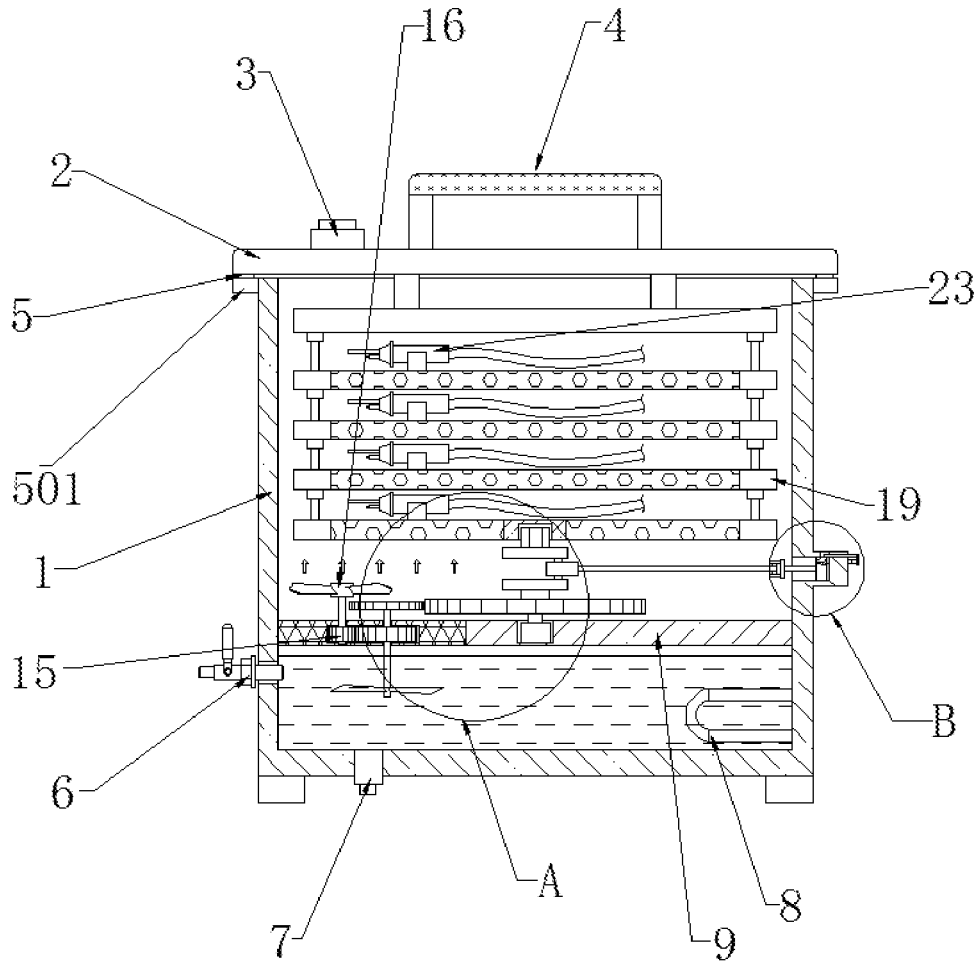
FIG. 1 is the schematic diagram of the main sectional structure of the disclosure.
Figure 2:
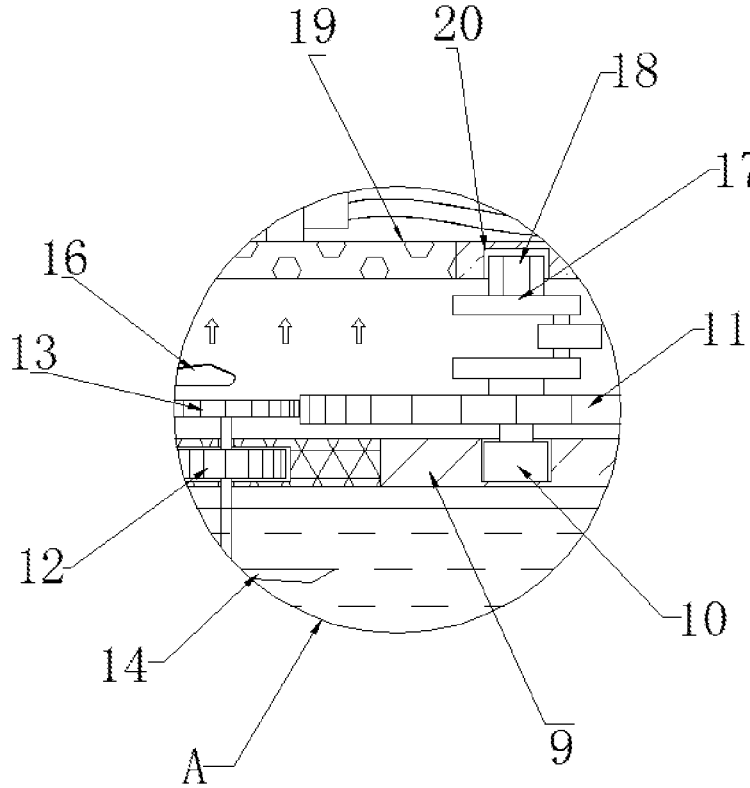
FIG. 2 is a schematic diagram of the enlarged structure at A in FIG. 1 of the present disclosure.
Figure 3:
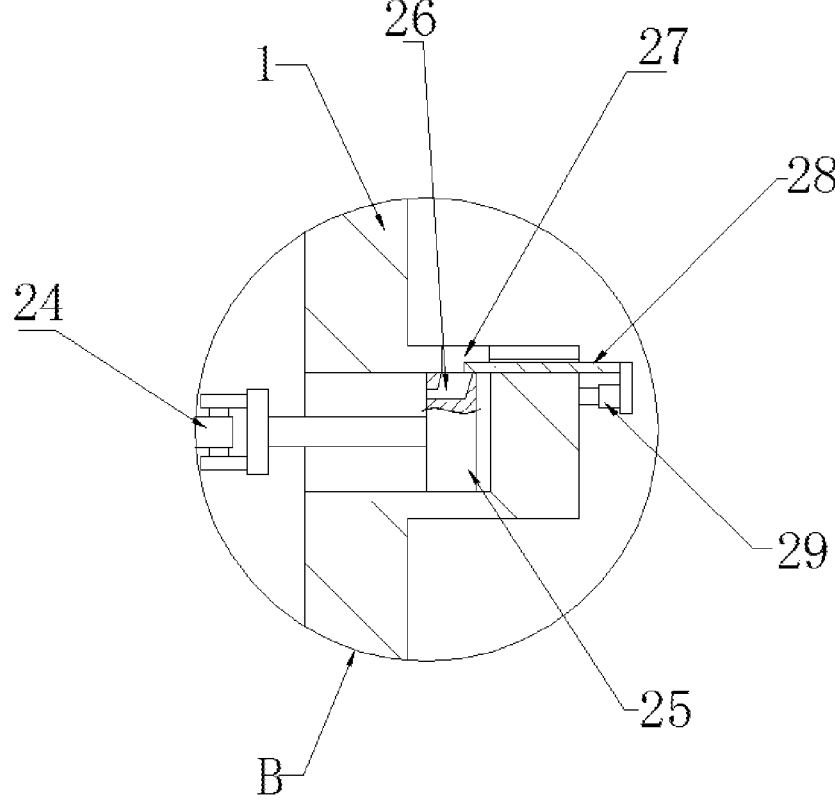
FIG. 3 is a schematic diagram of the enlarged structure at B in FIG. 1 of the present disclosure.
Figure 4:
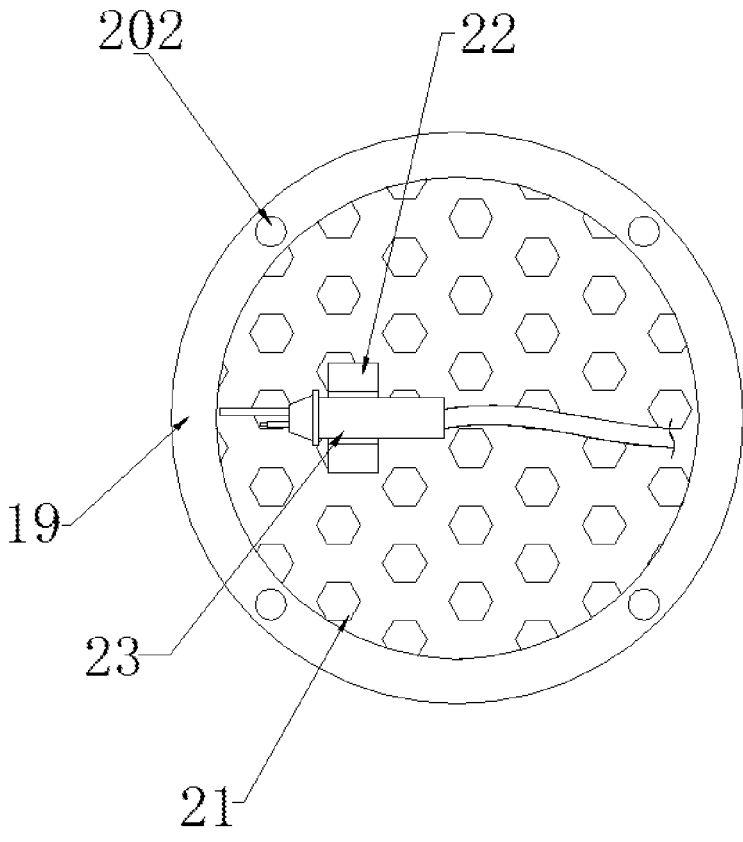
FIG. 4 is the schematic diagram of the top view structure of the support plate of the disclosure.
Figure 5:
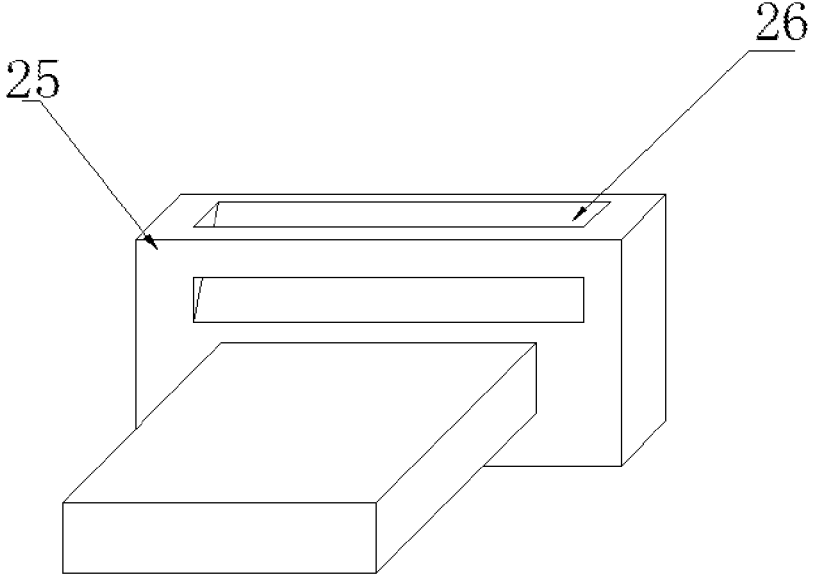
FIG. 5 is the schematic diagram of the three-dimensional structure of the piston of the disclosure.
Figure 6:
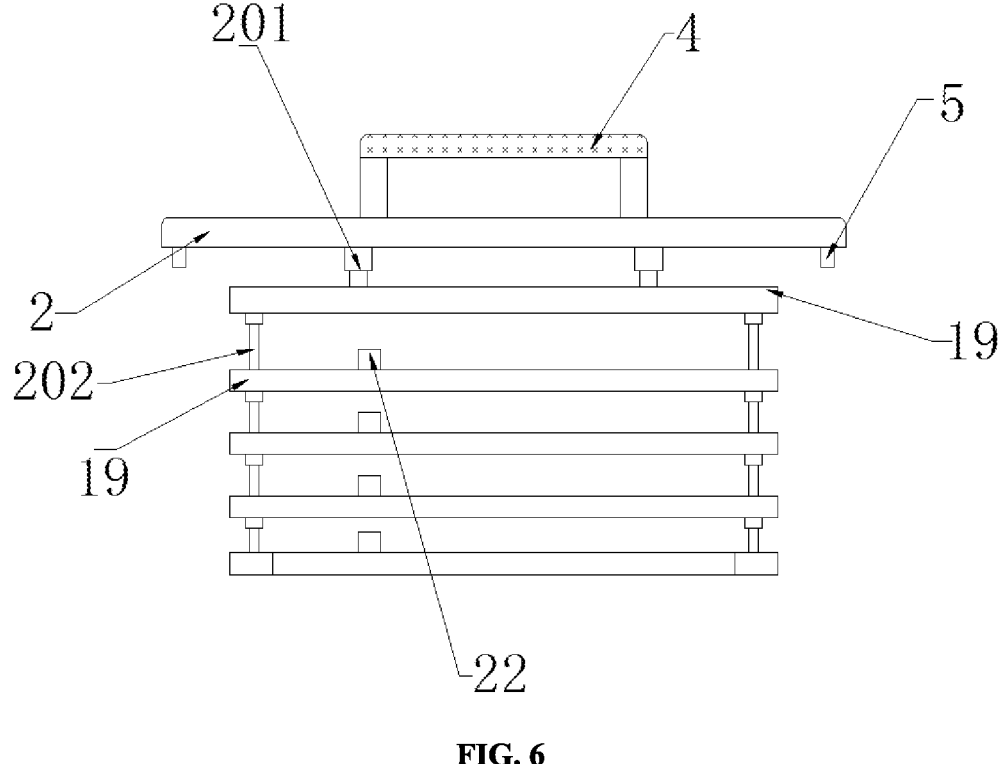
FIG. 6 is the schematic diagram of the main view structure of the top cover and the support plate of the disclosure.

Referring to FIG. 1 to FIG. 6, the disclosure provides a technical solution as follows. An energy-saving portable dryer for digestive endoscope includes a box 1 and a top cover 2. The box 1 is a hollow shell structure, and the top cover 2 covers the upper port of the box 1 to form a sealed environment. The upper end of the top cover 2 is provided with a controller 3 to control the operation of the device, and the box 1 is internally provided with heating tubes. The box 1 is provided with a water inlet and drainage mechanism. The bottom end of the box 1 is provided with a liquid heater 8, and the liquid heater 8 is arranged to heat a disinfection solution in the box 1 to generate hot vapor. The water inlet and drainage mechanism includes a water inlet valve 6 arranged at the lower side of the box 1 and a drainage valve 7 arranged at the bottom of the box 1. The water inlet valve 6 is opened to allow a proper amount of disinfection solution to enter the box 1. The disinfection solution should not overflow the partition 9. The liquid heater 8 heats the disinfection solution to generate the vapor. After sterilization, the drainage valve 7 discharges the disinfection solution.

The top cover 2 and the box 1 are installed and disassembled through a fixed mechanism. The fixed mechanism includes a first snap 5 arranged at the lower end of the top cover 2, and a second snap 501 at the side of the box 1 matched with the first snap 5, so that after the top cover 2 and the box 1 are combined, the first snap 5 and the second snap 501 form a self-locking structure. The handle 4 is held by hand, and the first snap 5 at the lower end of the top cover 2 is aligned with and inserted in the second snap 501 at the side of the box 1, so that the box 1 and the top cover 2 are closed to form a sealing environment.

The lower end of the top cover 2 is connected with support plates 19 through a telescopic mechanism, and an upper end of the support plate 19 is provided with a clamp 22 matched with a digestive endoscope 23. The clamp 22 is arranged to position the digestive endoscope 23, and the telescopic mechanism drives the support plate 19 to clamp the digestive endoscope 23 for positioning. The telescopic mechanism includes a first electric telescopic rod 201 connected with the lower end of the top cover 2, and the other end of the first electric telescopic rod 201 is connected with the support plate 19. The support plates 19 are connected to each other through a second electric telescopic rod 202. Multiple support plates 19 are provided. The bottom end of the support plate 19 at the lowest end is provided with a clamping groove 20, and the clamping groove 20 and a clamping column 18 at an upper end of a curved disc 17 are mutually matched and inserted. The clamping column 18 is a hexagonal prism, and the clamping groove 20 is a hexagonal groove. The surface of the support plate 19 is provided with a mesh 21 for through which the hot vapor passes. The clamp 22 is an inverted U-shaped block structure, the digestive endoscope 23 is a cylindrical structure, and the radius of the U-shaped part of the clamp 22 is greater than the cylindrical radius of the digestive endoscope 23. The upper end of the top cover 2 is provided with a handle 4, and the handle 4 is made of thermal insulation material with high temperature resistance. First, the digestive endoscopes 23 to be dried are placed on the clamps 22 at the upper end of the support plates 19 in turn. The controller 3 is operated to start the second electric telescopic rod 202, which makes the space between the support plates 19 smaller, so that the digestive endoscope 23 is clamped by the support plate 19 and the clamp 22. The handle 4 is held by hand, and the top cover 2 is aligned with the box 1 to make them combined, so that the box 1 and the top cover 2 are closed to form a sealing environment. The first electric telescopic rod 201 is slightly adjusted to move down until the clamping groove 20 at the bottom of the support plate 19 is engaged with the clamping column 18.

A partition 9 is also arranged inside the box 1, and a motor 10 is installed in the partition 9. The motor 10 is connected with a fan blade 16 and a mixing blade 14 through a driving mechanism to drive the fan blade 16 and the mixing blade 14 to rotate. The driving mechanism includes a first gear 11 connected with the shaft end of the motor 10, and the surface of the partition 9 is provided with a rotating hole, and the rotating hole is connected with a first gear shaft 12 and a second gear shaft 15 in a rotating manner. The lower end of the first gear shaft 12 is connected with the mixing blade 14, and the upper end of the first gear shaft 12 is connected with the second gear 13. The second gear 13 and the second gear shaft 15 form gear mesh. The upper end of the second gear shaft 15 is connected with the fan blade 16, and the first gear 11 and the second gear 13 form gear mesh. The motor 10 drives the first gear 11 to rotate, the first gear 11 drives the second gear 13 to rotate, and the second gear 13 drives the mixing blade 14 to stir the disinfection solution, making it more uniform. At the same time, the first gear shaft 12 drives the second gear shaft 15 to rotate, and the second gear shaft 15 drives the fan blade 16 to rotate. The hot vapor is drawn by the fan blade 16 from the air hole on the left side of the partition 9 to the upper inner end of the box 1. The vapor goes up through the mesh 21 to contact the digestive endoscope 23 for sterilization. The clamping column 18 drives the clamping groove 20 to rotate, and then drives the support plate 19 to rotate, so as to realize the all-round sterilization of the digestive endoscope 23 by hot vapor. When the sterilization is completed, the disinfection solution is discharged from the drainage valve 7.

The upper end of shaft of the motor 10 is provided with the curved disc 17, and the curved disc 17 and a crankshaft rod 24 form a reciprocating movement structure. The right end of the crankshaft rod 24 is provided with a piston 25 through a hinge. The surface of the box 1 is provided with an air hole 27, and the piston 25 moves laterally to open and close the air hole 27 intermittently to achieve intermittent pressure relief. The air hole 27 is provided with an opening size control mechanism to achieve the efficiency required for regulating the discharge of high-temperature and high-pressure gas. The opening size control mechanism includes a chute arranged on the side of the box 1, and a sealing plate 28 is arranged in the chute. The sealing plate 28 is located above the through hole 26 and contacts. One end of the sealing plate 28 is connected with the right end of the third electric telescopic rod 29, and the left end of the third electric telescopic rod 29 is connected with the side of the box 1. The third electric telescopic rod 29 drives the sealing plate 28 to slide laterally in the chute to adjust the size of the air hole 27 accordingly. The surface of the piston 25 is provided with a through hole 26 for gas to flow out of the air hole 27, and the air hole 27 is a square hole structure. During this period, the curved disc 17 drives the crankshaft rod 24 to move back and forth laterally, thus driving the piston 25 to move laterally. The pressure gas is discharged from the through hole 26 through the air hole 27. The third electric telescopic rod 29 is operated to adjust the position where the sealing plate 28 blocks the through hole 26, so as to realize the volume of gas discharged in each reciprocating.

Embodiment 2

The difference between this embodiment and embodiment 1 is as follows.

A pulley is arranged at the bottom of the box 1, and the handle 4 is arranged into a retractable and foldable structure, just like the structure of a trunk package. When moving, the handle 4 is pulled by hand to drag the pulley to move the device, which improves the portability and practicability of the device.

Working principle: when using energy-saving portable dryer for digestive endoscope, first, the required dry digestive endoscopes 23 are placed on the clamps 22 at the upper end of the support plates 19 in turn. The controller 3 is operated to start the second electric telescopic rod 202, making the space between the support plates 19 smaller, so that the digestive endoscope 23 is clamped by the support plate 19 and the clamp 22. The handle 4 is held by hand, and the first snap 5 at the lower end of the top cover 2 is aligned with and inserted in the second snap 501 at the side of the box 1, so that the box 1 and the top cover 2 are closed to form a sealing environment. The first electric telescopic rod 201 is slightly adjusted to move down until the clamping groove 20 at the bottom of the support plate 19 is engaged with the clamping column 18. The water inlet valve 6 is opened to allow a proper amount of disinfection solution to enter the box 1. The disinfection solution should not overflow the partition 9. The liquid heater 8 heats the disinfection solution to generate the vapor. At this time, the motor 10 drives the first gear 11 to rotate, the first gear 11 drives the second gear 13 to rotate, and the second gear 13 drives the mixing blade 14 to stir the disinfection solution, making it more uniform. At the same time, the first gear shaft 12 drives the second gear shaft 15 to rotate, and the second gear shaft 15 drives the fan blade 16 to rotate. The hot vapor is drawn by the fan blade 16 from the air hole on the left side of the partition 9 to the upper inner end of the box 1. The vapor goes up through the mesh 21 to contact the digestive endoscope 23 for sterilization. During this period, the curved disc 17 drives the crankshaft rod 24 to move back and forth laterally, thus driving the piston 25 to move laterally. The pressure gas is discharged from the through hole 26 through the air hole 27. The third electric telescopic rod 29 is operated to adjust the position where the sealing plate 28 blocks the through hole 26, so as to realize the volume of gas discharged in each reciprocating. At the same time, the clamping column 18 drives the clamping groove 20 to rotate, and then drives the support plate 19 to rotate, so as to realize the all-round sterilization of the digestive endoscope 23 by hot vapor. When the sterilization is completed, the disinfection solution is discharged from the drainage valve 7. The heating tubes on the inner wall of the box 1 start to heat up, so as to heat and dry the digestive endoscope 23. During this period, the piston 25 still reciprocates to realize pressure relief, so as to ensure that the pressure inside the box 1 is stable within a suitable range. The clamping column 18 drives the clamping groove 20 to rotate, and then drives the support plate 19 to rotate, so as to realize the full heating and drying of the digestive endoscope 23 by hot vapor. During transportation, the device can be lifted by holding handle 4. The structure is similar to that of an electric cooker, which is small and light. Only one motor 10 is set, which can drive the support plate 19 to rotate and simultaneously drive the piston 25 to reciprocate for pressure relief, thus achieving energy saving and high efficiency.

In this way, a series of work is completed. What is not described in detail in this specification belongs to the prior art known to those skilled in the art.

For those skilled in the art, it is obvious that the disclosure is not limited to the details of the above exemplary embodiments, and can be realized in other specific forms without departing from the spirit or basic features of the disclosure. Therefore, from any point of view, the embodiments should be regarded as exemplary and non-restrictive. The scope of the disclosure is defined by the appended claims rather than the above description, so it is intended to include all changes within the meaning and scope of the equivalent elements of the claims in the disclosure. Any reference mark in the claims shall not be regarded as limiting the claims involved.

What is claimed is:

1. An energy-saving portable dryer for digestive endoscope, comprising a box (1) and a top cover (2), wherein the box (1) is a hollow shell structure, the top cover (2) covers an upper port of the box (1) to form a sealed environment, an upper end of the top cover (2) is provided with a controller (3) to control an operation of the energy-saving portable dryer for digestive endoscope, and the box (1) is internally provided with heating tubes;

the box (1) is provided with a water inlet and drainage mechanism, a bottom end of the box (1) is provided with a liquid heater (8), and the liquid heater (8) is arranged to heat a disinfection solution in the box (1) to generate hot vapor;

the top cover (2) and the box (1) are installed and disassembled through a fixed mechanism;

a lower end of the top cover (2) is connected with a plurality of support plates (19) through a telescopic mechanism, and an upper end of each one of the plurality of support plates (19) is provided with a clamp (22) matched with a digestive endoscope (23); the clamp (22) is arranged to position the digestive endoscope (23), and the telescopic mechanism is configured to drive each support plate (19) to clamp the digestive endoscope (23) for positioning;

the plurality of the support plates (19) are provided, a bottom end of a support plate (19) at a lowest end is provided with a clamping groove (20), and the clamping groove (20) and a clamping column (18) at an upper end of a curved disc (17) are mutually matched and inserted;

a partition (9) is also arranged inside the box (1), a motor (10) is installed in the partition (9), and the motor (10) is connected with a fan blade (16) and a mixing blade (14) through a driving mechanism to drive the fan blade (16) and the mixing blade (14) to rotate;

an upper end of a shaft of the motor (10) is provided with the curved disc (17), and the curved disc (17) and a crankshaft rod (24) form a reciprocating movement structure; a right end of the crankshaft rod (24) is provided with a piston (25) through a hinge; a surface of the box (1) is provided with an air hole (27), and the piston (25) is configured to move laterally to open and close the air hole (27) intermittently to achieve intermittent pressure relief; and the air hole (27) is provided with an opening size control mechanism to achieve efficiency required for regulating discharge of high-temperature and high-pressure gas.

2. The energy-saving portable dryer for digestive endoscope of claim 1, wherein the water inlet and drainage mechanism comprises a water inlet valve (6) arranged at a lower side of the box (1) and a drainage valve (7) arranged at a bottom of the box (1).

3. The energy-saving portable dryer for digestive endoscope of claim 1, wherein the fixed mechanism comprises a first snap (5) arranged at the lower end of the top cover (2) and a second snap (501) at a side of the box (1) matched with the first snap (5), so that after the top cover (2) and the box (1) are combined, the first snap (5) and the second snap (501) form a self-locking structure.

4. The energy-saving portable dryer for digestive endoscope of claim 1, wherein the telescopic mechanism comprises first electric telescopic rods (201) connected with the lower end of the top cover (2), and other ends of the first electric telescopic rods (201) are connected with a support plate (19) close to the lower end of the top cover, and the plurality of support plates (19) are connected to each other through second electric telescopic rods (202); the clamping column (18) is a hexagonal prism, and the clamping groove (20) is a hexagonal groove, and a surface of each support plate (19) is provided with meshes (21) for through which the hot vapor passes.

5. The energy-saving portable dryer for digestive endoscope of claim 4, wherein the clamp (22) is an inverted U-shaped block structure, the digestive endoscope (23) is a cylindrical structure, and a radius of a U-shaped part of the clamp (22) is greater than a cylindrical radius of the digestive endoscope (23).

6. The energy-saving portable dryer for digestive endoscope of claim 5, wherein the upper end of the top cover (2) is provided with a handle (4), and the handle (4) is made of a thermal insulation material with high temperature resistance.

7. The energy-saving portable dryer for digestive endoscope of claim 1, wherein the driving mechanism comprises a first gear (11) connected with a shaft end of the motor (10), and a surface of the partition (9) is provided with a rotating hole, and the rotating hole is connected with a first gear shaft (12) and a second gear shaft (15) in a rotating manner; a lower end of the first gear shaft (12) is connected with the mixing blade (14), and an upper end of the first gear shaft (12) is connected with a second gear (13), and the second gear (13) and the second gear shaft (15) form gear mesh; an upper end of the second gear shaft (15) is connected with the fan blade (16), and the first gear (11) and the second gear (13) form gear mesh.

8. The energy-saving portable dryer for digestive endoscope of claim 1, wherein a surface of the piston (25) is provided with a through hole (26) for gas to flow out of the air hole (27), and the air hole (27) is a square hole structure.

9. The energy-saving portable dryer for digestive endoscope of claim 8, wherein the opening size control mechanism comprises a chute arranged on a side of the box (1), and a sealing plate (28) is arranged in the chute; the sealing plate (28) is located above the through hole (26) and contacts the surface of the piston; one end of the sealing plate (28) is connected with a right end of a third electric telescopic rod (29), and a left end of the third electric telescopic rod (29) is connected with the side of the box (1); the third electric telescopic rod (29) is configured to drive the sealing plate (28) to slide laterally in the chute to adjust a size of the air hole (27) accordingly.

* * * * *